US011253211B2

(12) United States Patent
Wang et al.

(10) Patent No.: US 11,253,211 B2
(45) Date of Patent: Feb. 22, 2022

(54) SYSTEM AND METHOD FOR UTILIZING AN X-RAY IMAGING SYSTEM HAVING A HYBRID DETECTOR

(71) Applicant: GE PRECISION HEALTHCARE LLC, Wauwatosa, WI (US)

(72) Inventors: Bo Wang, Beijing (CN); Hongye Zhang, Beijing (CN); Liang Zhang, Beijing (CN); Dayang Yuan, Beijing (CN)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 90 days.

(21) Appl. No.: 16/881,948

(22) Filed: May 22, 2020

(65) Prior Publication Data

US 2021/0361248 A1 Nov. 25, 2021

(51) Int. Cl.
*A61B 6/00* (2006.01)
*A61B 6/03* (2006.01)

(52) U.S. Cl.
CPC ............ *A61B 6/4266* (2013.01); *A61B 6/035* (2013.01); *A61B 6/4085* (2013.01)

(58) Field of Classification Search
CPC .................................................. A61B 6/4266
See application file for complete search history.

(56) References Cited

U.S. PATENT DOCUMENTS

| 6,842,502 B2 | 1/2005 | Jaffray et al. |
| 6,900,442 B2 | 5/2005 | Zur |
| 7,596,205 B2 * | 9/2009 | Zhang .................. A61B 6/0487 378/9 |
| 7,606,346 B2 | 10/2009 | Tkaczyk et al. |
| 9,042,513 B2 | 5/2015 | Shi et al. |

FOREIGN PATENT DOCUMENTS

CN 101919701 B 5/2012

* cited by examiner

*Primary Examiner* — Dani Fox
(74) *Attorney, Agent, or Firm* — Fletcher Yoder, P.C.

(57) ABSTRACT

A computed tomography (CT) imaging system is provided. The CT imaging system includes a gantry, rotatable about an axis of rotation. The CT imaging system also includes a table configured to move a subject to be imaged into and out of a bore of the gantry. The CT imaging system further includes a radiation source mounted on the gantry and configured to emit an X-ray beam. The CT imaging system even further includes one or more detectors configured to detect the emitted X-ray beam, wherein the one or more detectors comprises a flat panel detector disposed within the table, wherein the table is configured to move the flat panel detector into and out of the bore. The CT imaging system is configured to generate a two-dimensional image of the subject utilizing the radiation source and the flat panel detector.

20 Claims, 4 Drawing Sheets

SYSTEM AND METHOD FOR UTILIZING AN X-RAY IMAGING SYSTEM HAVING A HYBRID DETECTOR

BACKGROUND

The subject matter disclosed herein relates to medical imaging and, in particular, to utilizing a medical imaging system having a hybrid detector.

Non-invasive imaging technologies allow images of the internal structures or features of a patient to be obtained without performing an invasive procedure on the patient. In particular, such non-invasive imaging technologies rely on various physical principles, such as the differential transmission of X-rays through the target volume or the emission of gamma radiation, to acquire data and to construct images or otherwise represent the observed internal features of the patient.

Medical imaging systems, such as an X-ray imaging system (planar radiography) and a computed tomography (CT) imaging system are two distinct imaging systems. Typically, both the X-ray imaging system and the CT imaging system are maintained in separate rooms with dedicated equipment (e.g., power and control systems, collimator, X-ray source or tube, workstation, etc.). Although both the X-ray imaging system and the CT imaging system are utilized as diagnostic tools, there are key technical differences between them (e.g., regarding spatial resolution, afterglow or lag, source to image receptor distance, etc.) One key technical difference is that two-dimensional (2D) images are acquired with an X-ray imaging system while three-dimensional imaging volumes may be acquired with a CT imaging system. In addition, certain imaging workflows that utilize both types of imaging systems may be both costly and inconvenient.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In accordance with a first embodiment, a computed tomography (CT) imaging system is provided. The CT imaging system includes a gantry, rotatable about an axis of rotation. The CT imaging system also includes a table configured to move a subject to be imaged into and out of a bore of the gantry. The CT imaging system further includes a radiation source mounted on the gantry and configured to emit an X-ray beam. The CT imaging system even further includes one or more detectors configured to detect the emitted X-ray beam, wherein the one or more detectors comprises a flat panel detector disposed within the table, wherein the table is configured to move the flat panel detector into and out of the bore. The CT imaging system is configured to generate a two-dimensional image of the subject utilizing the radiation source and the flat panel detector.

In accordance with a second embodiment, a method is provided. The method includes acquiring a two-dimensional scout scan image of a subject utilizing a radiation source mounted on a gantry of a computed tomography (CT) imaging system and a flat panel detector disposed within a table of the CT imaging system that supports the subject. The method also includes determining, via control circuitry of the CT imaging system, if the scout scan image is sufficient for utilizing in diagnosis. The method further includes acquiring an imaging volume of the subject utilizing the radiation source and a detector assembly integrated within the gantry of the CT imaging system when the scout scan image is not sufficient for utilizing in diagnosis.

In accordance with a third embodiment, an X-ray imaging system is provided. The X-ray imaging system includes a gantry, rotatable about an axis of rotation. The X-ray imaging system also includes a table configured to move a subject to be imaged into and out of a bore of the gantry. The X-ray imaging system further includes a radiation source mounted on the gantry and configured to emit an X-ray beam. The X-ray imaging system even further includes a hybrid detection system configured to detect the emitted X-ray beam. The hybrid detection system includes a flat panel detector disposed within the table, wherein the table is configured to move the flat panel detector into and out of the bore. The hybrid detection system also includes a CT detector assembly integrated within the gantry. The CT imaging system is configured to generate a two-dimensional image of the subject utilizing the radiation source and the flat panel detector and an imaging volume of the subject utilizing the radiation source and the CT detector assembly.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
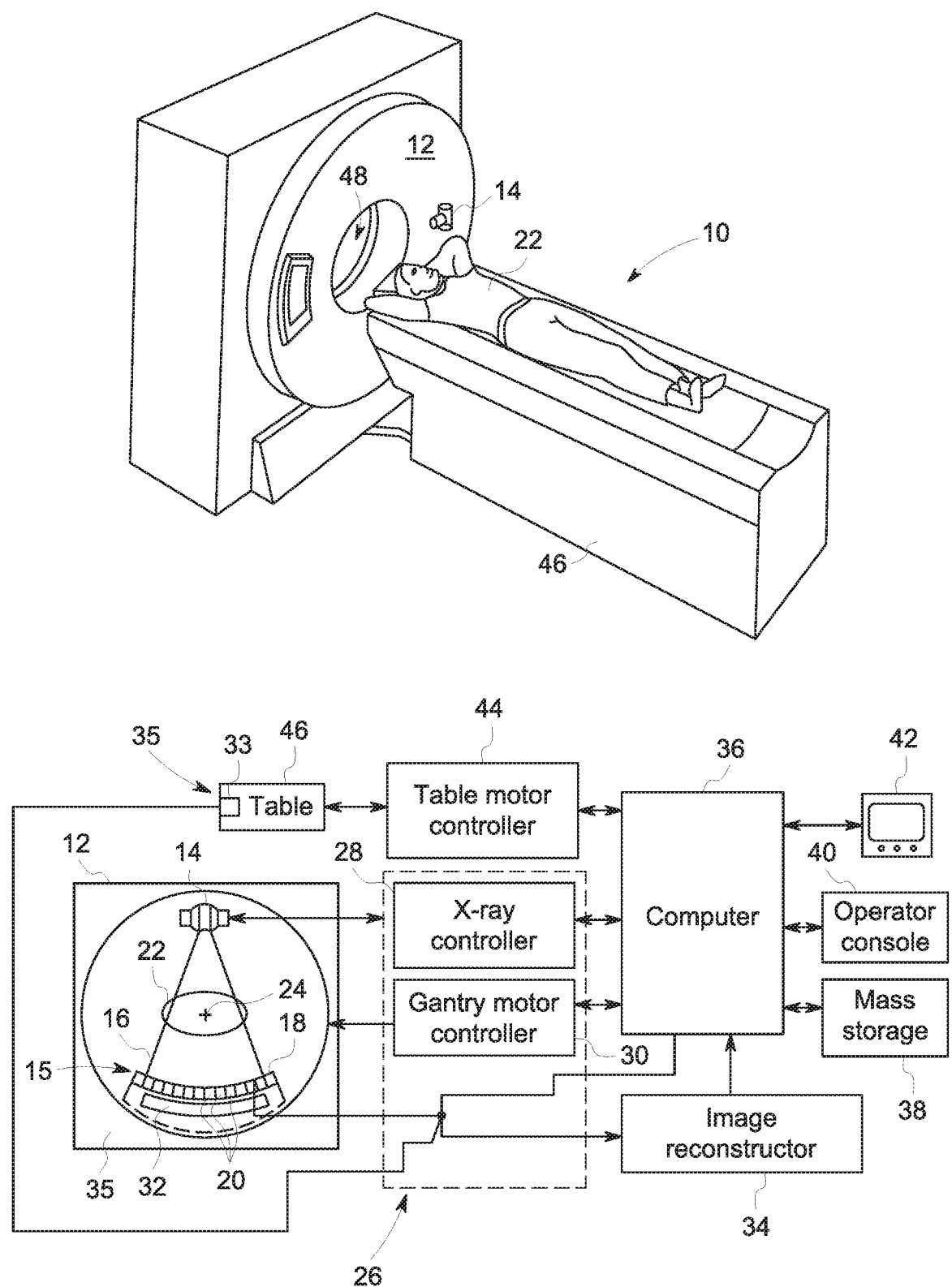
FIG. 1 is a combined pictorial view and block diagram of an embodiment of a computed tomography (CT) imaging system as discussed herein.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The presently contemplated embodiments provide a medical imaging system that utilizes a hybrid detector. In particular, the imaging system may be utilized for conventional X-ray imaging (e.g., planar radiography) and CT imaging. For example, a radiation source (e.g., X-ray tube) may be coupled to a gantry of a CT imaging system and utilized with different detectors depending on the type of imaging utilized. One detector may include a CT detector assembly integrated within the gantry that is utilized during CT imaging (e.g., to generate a 3D imaging volume). Another detector includes a flat panel detector disposed within (e.g., inserted within a slot) of a table of the CT imaging system that is utilized during conventional X-ray imaging (e.g., to generate a 2D image). A control system of the imaging system may automatically switch between the different imaging scan modes (conventional X-ray imaging and CT imaging). In certain imaging workflows, the imaging system may utilize the conventional X-ray imaging scan mode to generate a scout scan. The control system may then determine based on if the scout scan is sufficient for diagnostic purposes whether or not to switch to CT imaging scan mode to acquire further image data. For example, if the scout scan is not sufficient for diagnostic purposes, the imaging system will switch to CT imaging scan mode to acquire CT scan data (e.g., via an axial or helical scan). The imaging system enables the different imaging modalities to share components (e.g., radiation source, collimator, power and control systems, workstation, etc.), which provides improved imaging system performance, convenience for patients, cost reduction, while also saving space.

Although the following embodiments are discussed in terms of a computed tomography (CT) imaging system, the embodiments may also be utilized with other imaging systems (e.g., PET, CT/PET, SPECT, nuclear CT, etc.). With the preceding in mind and referring to FIG. 1, a CT imaging system 10 is shown, by way of example. As described in greater detail below, the CT imaging system 10 may be utilized in a conventional X-ray imaging scan mode (e.g., utilizing a flat panel detector) or a CT imaging scan mode (e.g., utilizing detector assembly 15). The depicted CT imaging system may be housed within a single room. The CT imaging system includes a gantry 12. The gantry 12 has an X-ray source 14 that projects a beam of X-rays 16 toward a detector assembly 15 (e.g., CT detector assembly) on the opposite side of the gantry 12 in a CT imaging scan mode. The detector assembly 15 includes a collimator assembly 18, a plurality of detector modules 20, and data acquisition systems (DAS) 32. The plurality of detector modules 20 detect the projected X-rays that pass through a patient 22, and DAS 32 converts the data to digital signals for subsequent processing. Each detector module 20 in a conventional system produces an analog electrical signal that represents the intensity of an incident X-ray beam and hence the attenuated beam as it passes through the patient 22. During a CT scan to acquire X-ray projection data, gantry 12 and the components mounted thereon rotate about a center of rotation 24 so as to collect attenuation data from a multitude of view angles relative to the imaged volume.

The imaging system 10 also includes a solid-state detector such as a digital flat panel detector 33 (e.g., inserted in a table 46) for utilization with the radiation source 14 during a conventional X-ray imaging scan mode (e.g., planar radiography) to acquire image data for generating a 2D image. The flat panel detector 33 may be an indirect detector (e.g., utilizing a scintillator to convert X-rays into light) or a direct detector (e.g., utilizing photoconductors to convert incident X-ray photons into electric charge). The flat panel detector 33 may be coupled via wired (e.g., tethered) or wireless connection to transmit image data. In certain embodiment, the wired connection may be utilized to provide power to the flat panel detector 33. Together, the flat panel detector 33 and the CT detector assembly 15 form a hybrid detector system 35.

Rotation of gantry 12 and the operation of X-ray source 14 are governed by a control mechanism 26 of CT system 10. Control mechanism 26 includes an X-ray controller 28 that provides power and timing signals to an X-ray source 14 and a gantry motor controller 30 that controls the rotational speed and position of gantry 12. An image reconstructor 34 receives sampled and digitized X-ray data from DAS 32 and performs high-speed reconstruction. The reconstructed image is applied as an input to a computer 36, which stores the image in a mass storage device 38. Computer 36 also receives commands and scanning parameters from an operator via console 40. An associated display 42 allows the operator to observe the reconstructed image and other data from computer 36. The operator supplied commands and parameters are used by computer 36 to provide control signals and information to DAS 32, X-ray controller 28, and gantry motor controller 30. In addition, computer 36 operates a table motor controller 44, which controls a motorized table 46 (and/or patient support such as a cradle) to position patient 22 relative to the gantry 12. Particularly, table 46 moves (e.g., extends) portions of patient 22 on the patient support through a gantry opening or bore 48. In addition, the table motor controller 44 may control movement of the flat panel detector 33 (e.g., via movement of a compartment (see compartment 50 in FIG. 2) where the flat panel detector 33 is disposed within the table 46) into and out of the bore 48. Components of the CT imaging system 10 may be utilized in both the conventional X-ray imaging scan mode and the CT imaging scan mode. For example, in either mode X-ray source 14, collimator assembly 18, control mechanism 26, computer 36, console 40, display 42, and table motor controller 44, among other components. As described in greater detail below, the control mechanism may be utilized to automatically switch between the conventional X-ray imaging scan mode and the CT imaging scan mode based on certain criteria (e.g., whether a scout scan acquired in the conventional X-ray imaging scan mode is sufficient for utilizing in diagnostics).

Figure 2:
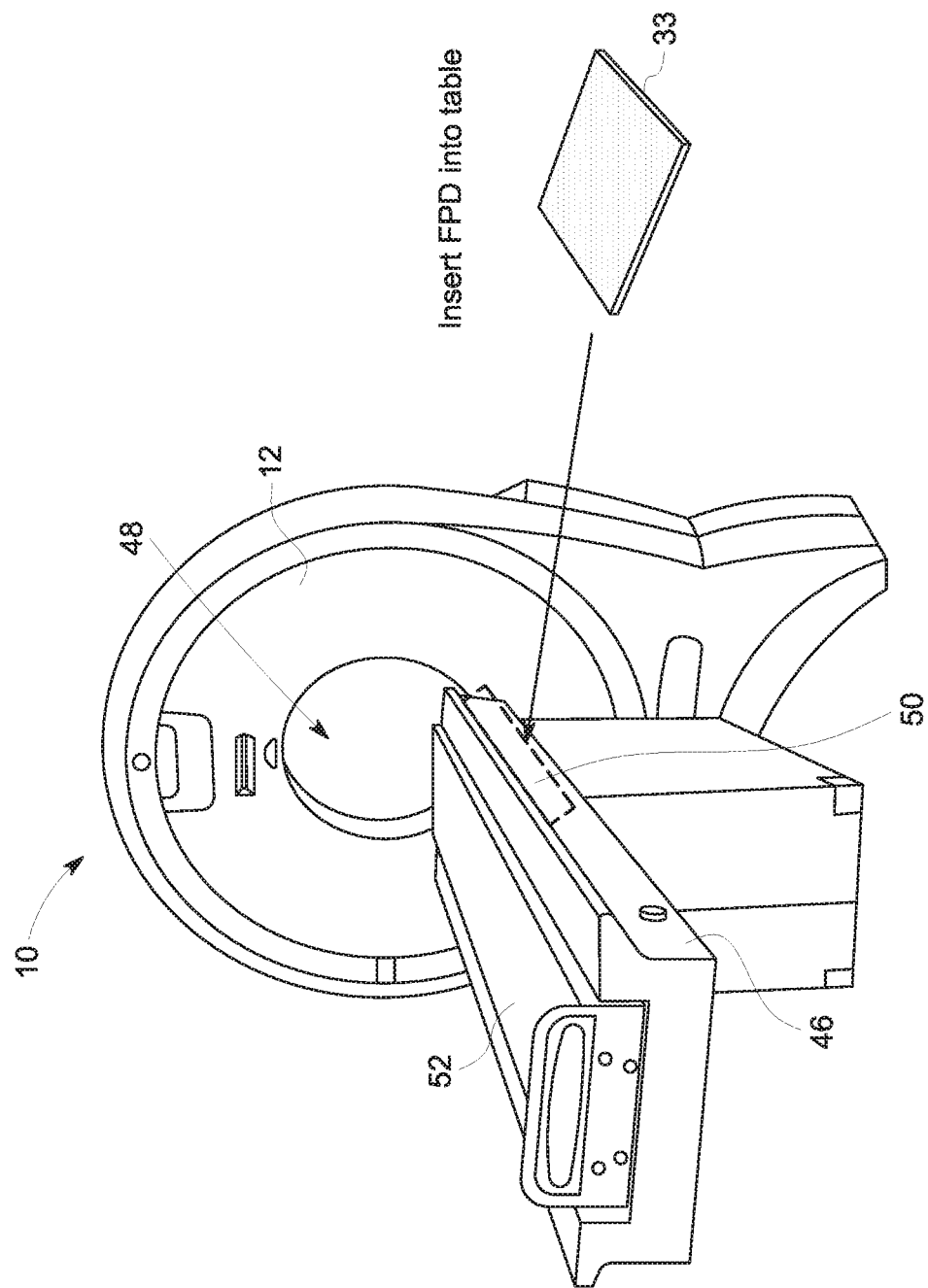
FIG. 2 is a schematic diagram of an embodiment of a flat panel detector being inserted within a table of the CT imaging system of FIG. 1.

FIG. 2 is a schematic diagram of the flat panel detector 33 being inserted within the table 46 of the CT imaging system 10 of FIG. 1. The CT imaging system 10 is as described above in FIG. 1. The table 46 includes a compartment 50 defined by the table 46 that is configured to receive the flat panel detector 33 within. The compartment 50 is configured to receive flat panel detectors 33 of different sizes. The compartment 50 is located below a patient support 52 that supports the patient or the subject to be imaged. The flat panel detector 33 may be secured within the compartment via one or more fasteners.

Figure 3:
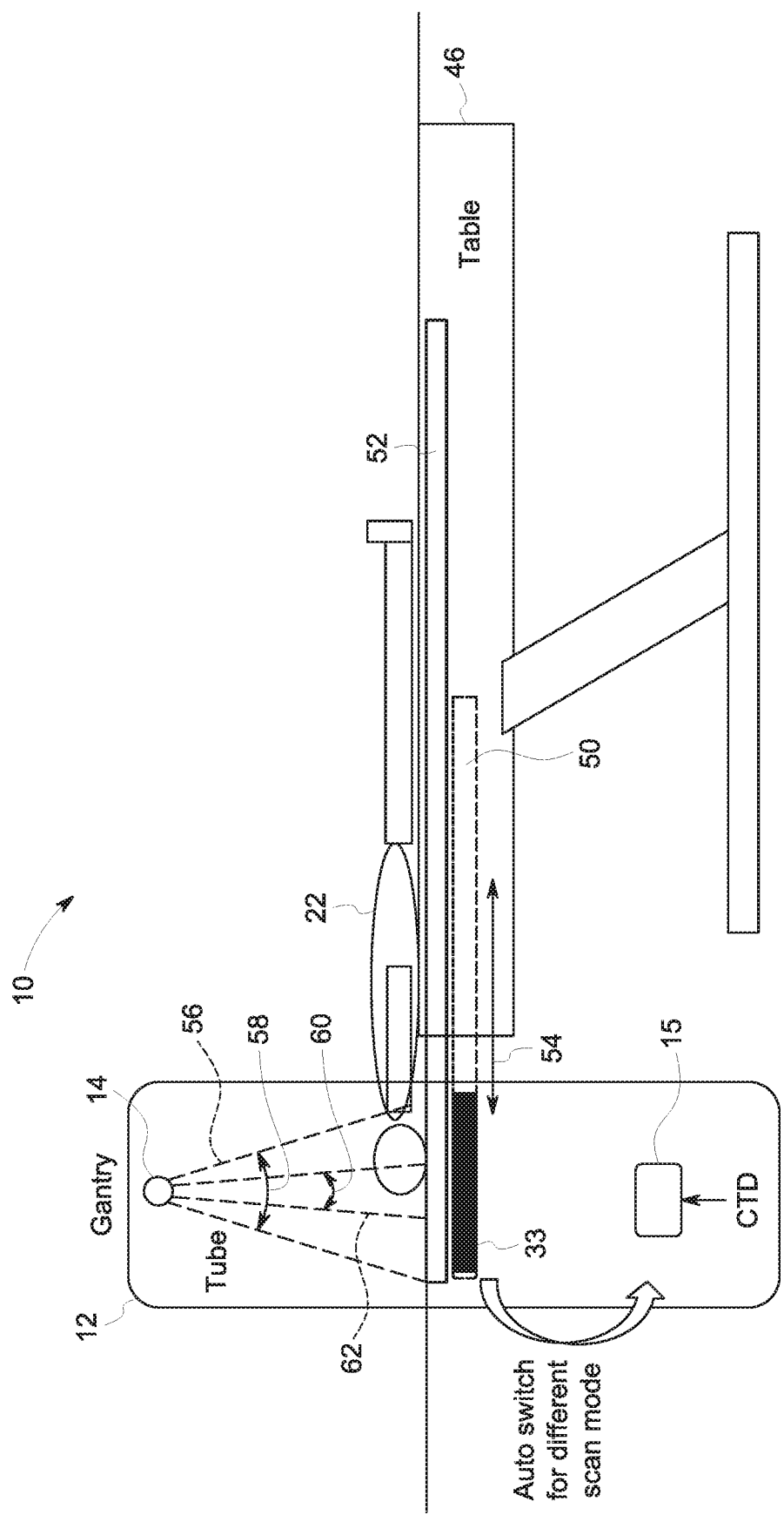
FIG. 3 is a schematic diagram of movement of a patient and/or a flat panel detector within a bore of a gantry.

FIG. 3 is a schematic diagram of movement of the patient 22 and/or the flat panel detector 33 within the bore 48 of the gantry 12. The table 46 is configured (e.g., via the table motor controller 44) to move the patient 22 into and out of the bore 48 of the gantry 12 via the movement of the patient support 52 as indicated by the arrows 54. The table 46 is also configured to move the flat panel detector 33 (along with at least a portion of the compartment 50) into and out of the bore 48 of the gantry 12 (e.g., via the table motor controller 44). The table 46 is configured to move the flat panel detector 33 independent of the patient support 52 (and, thus, the patient 22). In certain embodiments, the compartment 50 may be coupled to a mechanical mechanism (e.g., coupled to a motor) that controls the extension and retraction of the compartment 50 and, thus, the movement of the flat panel detector 33. In an X-ray imaging scan mode, the flat pane detector 33 is disposed within the bore 48 as depicted in FIG. 3. In the CT imaging scan mode, the flat panel detector 33 is disposed outside of the bore 48 and the CT detector 15 is utilized during imaging.

As depicted in FIG. 3, the radiation source 14 (e.g., X-ray tube) is configured or optimized to emit an X-ray beam 56 at an angle 58 wide enough to cover an entire active area of the flat panel detector 33. The angle 58 is wider than an angle 60 of an X-ray beam 62 typically utilized when performing imaging with the CT detector 15.

Figure 4:
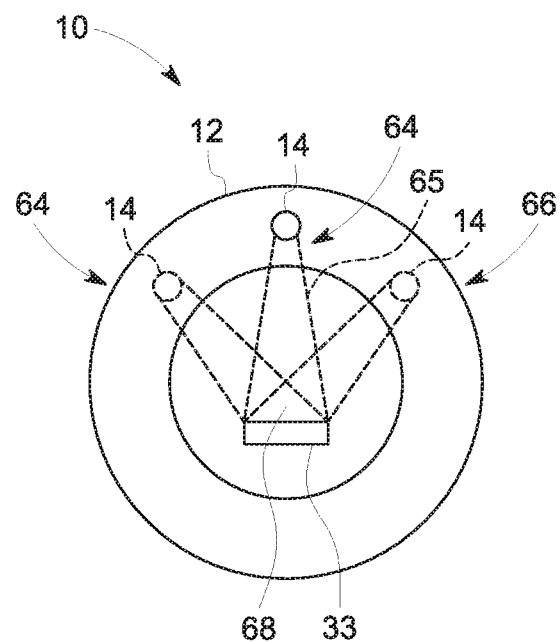
FIG. 4 is a schematic diagram illustrating a position of a radiation source relative to a flat panel detector during a conventional X-ray imaging scan.

FIG. 4 is a schematic diagram illustrating a position of the radiation source 14 relative to the flat panel detector 33 during a conventional X-ray imaging scan. In a typical conventional X-ray imaging position indicated by arrow 64, the radiation source 14 is located directly above (e.g., dead top center) the flat panel detector 33 when emitting the X-ray beam 65. In certain embodiments during a conventional X-ray imaging scan, the radiation source 14 may be rotated via the gantry to a position 64, 66 that circumferentially offset (e.g., relative to an axis of rotation 22 (see FIG. 2) of the gantry 14) from the dead top center position 64. In these positions 64, 66, as depicted, a surface 68 that receives the radiation may remain parallel relative to the ground or a top surface of the table 46 (see FIG. 3). In certain embodiments, when the radiation source 14 is utilized in a position (e.g., positions 64, 66) that is not the top dead center position 64, the position of the detector may angled (manually or automatically) via a mechanism within the compartment 50 to angle the detector 33 (e.g., surface 68) so that it directly faces the radiation source 14.

Figure 5:
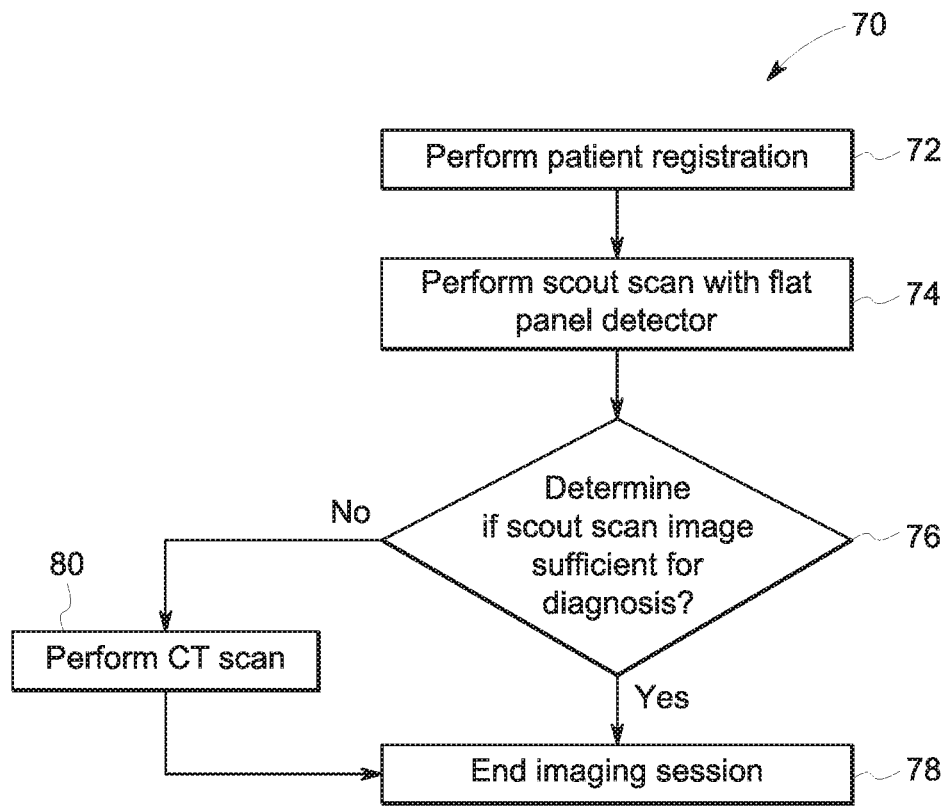
FIG. 5 is a flow chart of an embodiment of a method for performing an imaging scan workflow.

FIG. 5 is a flow chart of an embodiment of a method 70 for performing an imaging scan workflow. One or more steps of the method 70 may be performed by one or more components of the imaging system 10 (e.g., control mechanism 26, table motor controller 44, computer 36, etc.). One or more of the steps of the method 70 may be performed simultaneously and/or in a different order from that illustrated in FIG. 5. The method 70 includes performing, prior to acquiring a two-dimensional scout scan image, registering a position of the patient 22 relative to the CT imaging system 10 (block 72). Patient registration may occur utilizing techniques known in the art. In certain embodiments, patient registration may be performing one or more scout scan utilizing the CT detector 15. Scout scans utilize a radiation dose from the radiation source 14 that is lower than typically utilized during a CT imaging scan used to acquire diagnostic information. The method 72 also includes performing a scout scan (in the conventional X-ray imaging mode) utilizing the flat panel detector 33 in conjunction with the radiation source 14 (block 74). The radiation source 14 in the conventional X-ray imaging mode may be located in a top dead center position above the flat panel detector or circumferentially offset from the top dead center position as described above in FIG. 4. A 2D scout scan image is acquired from the scout scan. The scout scan image with the flat panel detector 33 is acquired utilizing a radiation dose that is higher than a scout scan performed in a CT imaging scan but less than a radiation dose utilized in a CT imaging scan for diagnostic purposes (as opposed to a scout scan acquired in CT imaging scan mode). The scout scan image acquired with the flat panel detector 33 has a higher spatial resolution than a scout scan image acquired in the CT imaging scan mode and, thus, may be utilized for diagnostic purposes. The method 70 includes determining (e.g., via control circuitry of the imaging system 10) whether the scout scan image acquired in the conventional X-ray imaging mode is sufficient for diagnostic purposes (block 76). If the scout scan image acquired in the conventional X-ray imaging mode is sufficient for diagnostic purposes, the imaging session ends (block 78). If the scout scan image acquired in the conventional X-ray imaging mode is sufficient for diagnostic purposes, the control circuitry switches into CT imaging scan mode (i.e., withdrawing the flat panel detector 33 from the bore 48 of the gantry 12) and the method 70 includes performing a CT imaging scan to acquire imaging data to generate an imaging volume (e.g., one or more 3D images) for diagnostic purposes (block 80). The CT imaging scan may be an axial or helical scan.

Technical effects of the disclosed embodiments include providing a medical imaging system that includes a hybrid detection system. The medical imaging system may be utilized in a conventional X-ray imaging scan mode or a CT imaging scan mode. The hybrid detection system includes a flat panel detector (e.g., for utilization in conventional imaging scan mode) that can be moved in and out of a bore of a gantry of the medical imaging system. In addition, the hybrid detection system includes a CT detector assembly (e.g., for utilization in CT imaging scan mode). The medical imaging system enables the different imaging modalities to share components (e.g., radiation source, collimator, power and control systems, workstation, etc.), which provides improved imaging system performance, convenience for patients, cost reduction, while also saving space.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computed tomography (CT) imaging system, comprising:
   a gantry, rotatable about an axis of rotation;
   a table configured to move a subject to be imaged into and out of a bore of the gantry;
   a radiation source mounted on the gantry and configured to emit an X-ray beam; and
   one or more detectors configured to detect the emitted X-ray beam, wherein the one or more detectors comprises a flat panel detector disposed within the table, wherein the table is configured to move the flat panel detector into and out of the bore;
   wherein the CT imaging system is configured to generate a two-dimensional image of the subject utilizing the radiation source and the flat panel detector.

2. The CT imaging system of claim 1, wherein the table is configured to move the flat panel detector independent of the subject.

3. The CT imaging system of claim 1, wherein the radiation source is configured to emit the X-ray beam at an angle wide enough to cover an entire active area of the flat panel detector.

4. The CT imaging system of claim 1, wherein the table is configured to accommodate flat panel detectors of different sizes within the table.

5. The CT imaging system of claim 1, wherein the flat panel detector is configured to communicate acquired image data via a wired connection or a wireless connection to the CT imaging system.

6. The CT imaging system of claim 1, wherein the radiation source is configured to emit the X-ray beam from a position directly above the flat panel detector.

7. The CT imaging system of claim 1, wherein the radiation source is configured to emit the X-ray beam toward the flat panel detector at different circumferential positions relative to the axis of rotation.

8. The CT imaging system of claim 1, wherein the one or more detectors comprises a CT detector assembly integrated within the gantry.

9. The CT imaging system of claim 8, wherein the CT imaging system is configured to generate an imaging volume of the subject utilizing the radiation source and the CT detector assembly.

10. The CT imaging system of claim 8, wherein the CT imaging system comprises control circuitry configured to automatically switch the CT imaging system between a first imaging scan mode that utilizes the flat panel detector and a second imaging scan mode that utilizes the CT detector assembly.

11. The CT imaging system of claim 8, wherein the control circuitry is configured to automatically switch from the first imaging mode to the second mode based on whether a scout scan image acquired in the first imaging mode is sufficient for utilizing in diagnosis.

12. The CT imaging system of claim 11, wherein the control circuitry is configured to switch to the second imaging mode from the first imaging mode when the scout scan image is not sufficient for utilizing in diagnosis.

13. A method, comprising:
acquiring a two-dimensional scout scan image of a subject utilizing a radiation source mounted on a gantry of a computed tomography (CT) imaging system and a flat panel detector disposed within a table of the CT imaging system that supports the subject;
determining, via control circuitry of the CT imaging system, if the scout scan image is sufficient for utilizing in diagnosis; and
acquiring an imaging volume of the subject utilizing the radiation source and a detector assembly integrated within the gantry of the CT imaging system when the scout scan image is not sufficient for utilizing in diagnosis.

14. The method of claim 13, comprising, prior to acquiring the two-dimensional scout scan image, registering a position of the subject relative to the CT imaging system.

15. The method of claim 13, comprising, prior to acquiring the two-dimensional scout scan image, moving the subject into a bore of the gantry via the table and moving, independent of movement of the subject, the flat panel detector via the table.

16. The method of claim 13, wherein acquiring the two-dimensional scout scan image comprises emitting an X-ray beam from the radiation source from a position directly above the flat panel detector.

17. The method of claim 13, wherein acquiring the two-dimensional scout scan image comprises emitting an X-ray beam from the radiation source toward the flat panel detector at a circumferential position relative to an axis of rotation of the gantry that is not directly above the flat panel detector.

18. The method of claim 13, wherein acquiring the two-dimensional scout scan image comprises emitting an X-ray beam from the radiation source toward the flat panel detector at an angle wide enough to cover an entire active area of the flat panel detector.

19. An X-ray imaging system, comprising:
a gantry, rotatable about an axis of rotation;
a table configured to move a subject to be imaged into and out of a bore of the gantry;
a radiation source mounted on the gantry and configured to emit an X-ray beam; and
a hybrid detection system configured to detect the emitted X-ray beam, wherein the hybrid detection system comprises:
a flat panel detector disposed within the table, wherein the table is configured to move the flat panel detector into and out of the bore; and
a CT detector assembly integrated within the gantry;
wherein the CT imaging system is configured to generate a two-dimensional image of the subject utilizing the radiation source and the flat panel detector and an imaging volume of the subject utilizing the radiation source and the CT detector assembly.

20. The X-ray imaging system of claim 19, comprising control circuitry configured to automatically switch the X-ray imaging system between a first imaging scan mode that utilizes the flat panel detector and a second imaging scan mode that utilizes the CT detector assembly.

* * * * *